US010152793B2

United States Patent
Jo et al.

(10) Patent No.: US 10,152,793 B2
(45) Date of Patent: Dec. 11, 2018

(54) MAGNETIC RESONANCE IMAGE PROCESSING METHOD AND MAGNETIC RESONANCE IMAGE PROCESSING APPARATUS

(71) Applicant: SAMSUNG ELECTRONICS CO., LTD., Suwon-si (KR)

(72) Inventors: Hyun-hee Jo, Osan-si (KR); Praveen Gulaka, Suwon-si (KR); Yang-lim Choi, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 9 days.

(21) Appl. No.: 15/329,007

(22) PCT Filed: Jun. 23, 2015

(86) PCT No.: PCT/KR2015/006379
§ 371 (c)(1),
(2) Date: Jan. 25, 2017

(87) PCT Pub. No.: WO2016/013773
PCT Pub. Date: Jan. 28, 2016

(65) Prior Publication Data
US 2017/0213341 A1 Jul. 27, 2017

(30) Foreign Application Priority Data
Jul. 25, 2014 (KR) .................. 10-2014-0095012

(51) Int. Cl.
*G06K 9/00* (2006.01)
*G06T 7/00* (2017.01)
(Continued)

(52) U.S. Cl.
CPC .......... *G06T 7/0016* (2013.01); *A61B 5/0044* (2013.01); *A61B 5/055* (2013.01);
(Continued)

(58) Field of Classification Search
CPC ......... G06T 7/00; G06T 7/0016; G06T 7/143; G06T 7/13; G06T 7/248; G06T 7/0012;
(Continued)

(56) References Cited

U.S. PATENT DOCUMENTS 5,903,664 A 5/1999 Hartley et al.
6,346,124 B1 * 2/2002 Geiser .................. G06T 7/0012
600/450
(Continued)

FOREIGN PATENT DOCUMENTS

JP 3176652 B2 6/2001
WO 2010/023618 A1 3/2010

OTHER PUBLICATIONS

Communication dated Oct. 16, 2015, issued by the Korean Intellectual Property Office in counterpart Korean application No. 10-2014-0095012.
(Continued)

*Primary Examiner* — Jose L Couso
(74) *Attorney, Agent, or Firm* — Sughrue Mion, PLLC

(57) ABSTRACT

Provided are a magnetic resonance (MR) image processing method and an MR image processing apparatus. The MR image processing apparatus includes: a signal transceiver that transmits or receives a signal to or from the heart; and an image processor that obtains a plurality of MR images of the heart by using the transmitted or received signal, determines at least one contour from each of the plurality of MR images; obtains first information about a first region formed by the at least one contour; and detects an apex MR image or a base MR image of the heart from among the plurality of MR images based on the first information, wherein a location of an apex or a base is automatically detected from a plurality of short-axis MR images of the heart.

15 Claims, 12 Drawing Sheets

(51) Int. Cl.
*A61B 5/055* (2006.01)
*A61B 5/00* (2006.01)
*G06T 7/143* (2017.01)
*G06T 7/13* (2017.01)
*G06T 7/246* (2017.01)

(52) U.S. Cl.
CPC ............... *G06T 7/13* (2017.01); *G06T 7/143* (2017.01); *G06T 7/248* (2017.01); *A61B 2576/023* (2013.01); *G06T 2207/10088* (2013.01); *G06T 2207/30048* (2013.01)

(58) Field of Classification Search
CPC ... G06T 7/11; G06T 7/149; G06T 7/12; G06T 7/62; G06T 7/162; G06T 7/33; G06T 19/20; G06T 2207/30048; G06T 2207/10072; G06T 2207/10132; G06T 2207/10076; G06T 2207/10081; G06T 2207/20012; G06T 2207/20101; G06T 2207/20116; G06T 2207/20168; G06T 2207/10088–2207/10096; G06T 2200/24; G06T 2210/41; A61B 5/0044; A61B 5/0456; A61B 5/05; A61B 5/055; A61B 5/0263; A61B 5/0037; A61B 5/02; A61B 5/0205–5/021; A61B 5/024–5/02405; A61B 5/222; A61B 6/00; A61B 6/03; A61B 6/503; A61B 6/5247; A61B 8/00; A61B 8/0883; A61B 8/02; A61B 8/065; A61B 2090/364; A61B 2090/3954; A61B 2018/00351–2018/00369; A61B 2576/00–2576/023; G01R 33/54; G01R 33/543; G01R 33/20; G01R 33/546; G01R 33/48; G01R 33/4833; G01R 33/4835; G01R 33/5608; G06K 9/6207; G06K 9/00; G06K 9/72; G06K 2209/00939; G06F 19/321; A61K 49/06; Y10S 128/922

See application file for complete search history.

(56) References Cited

U.S. PATENT DOCUMENTS

| | | | |
|---|---|---|---|
| 7,280,862 B2 * | 10/2007 | Gupta | A61B 5/055 600/407 |
| 7,603,154 B2 | 10/2009 | Noble et al. | |
| 7,678,052 B2 | 3/2010 | Torp et al. | |
| 7,966,055 B2 | 6/2011 | Guehring et al. | |
| 8,218,849 B2 * | 7/2012 | Lu | G06K 9/72 382/131 |
| 8,280,136 B2 | 10/2012 | Gotardo et al. | |
| 8,463,008 B2 | 6/2013 | Ciofolo-Veit et al. | |
| 9,314,161 B2 * | 4/2016 | Wang | A61B 5/0044 |
| 2002/0156359 A1 * | 10/2002 | Knoplioch | A61B 6/032 600/407 |
| 2005/0033143 A1 * | 2/2005 | O'Donnell | G06T 7/70 600/407 |
| 2007/0253609 A1 | 11/2007 | Aben | |
| 2008/0298682 A1 | 12/2008 | Cocosco et al. | |
| 2009/0149734 A1 * | 6/2009 | Sugiura | A61B 5/055 600/410 |
| 2010/0215238 A1 | 8/2010 | Lu et al. | |
| 2012/0082352 A1 * | 4/2012 | Hundley | A61B 5/055 382/128 |
| 2012/0101368 A1 * | 4/2012 | Masumoto | A61B 6/503 600/420 |
| 2012/0207371 A1 | 8/2012 | Wakai et al. | |
| 2014/0219524 A1 * | 8/2014 | Takeguchi | A61B 6/463 382/128 |
| 2015/0150454 A1 * | 6/2015 | Nitta | A61B 5/0044 324/309 |
| 2015/0153434 A1 * | 6/2015 | Ooshima | G01R 33/5676 324/309 |
| 2017/0127972 A1 * | 5/2017 | Kuhara | A61B 5/055 |

OTHER PUBLICATIONS

Communication dated Jan. 21, 2016, issued by the Korean Intellectual Property Office in counterpart Korean application No. 10-2014-0095012.

International Search Report (PCT/ISA/210) and Written Opinion (PCT/ISA/237) dated Sep. 24, 2015 issued by the International Searching Authority in counterpart International Application No. PCT/KR2015/006379.

Communication dated Nov. 28, 2017, from the European Patent Office in counterpart European Application No. 15825020.9.

K. Emilsson et al., "Outer Contour and radial changes of the cardiac left ventricle; A magnetic resonance imaging study", Original Paper, Clinical Research in Cardiology, vol. 96, No. 5, (2007) (pp. 272-278, 8 Pages Total).

* cited by examiner

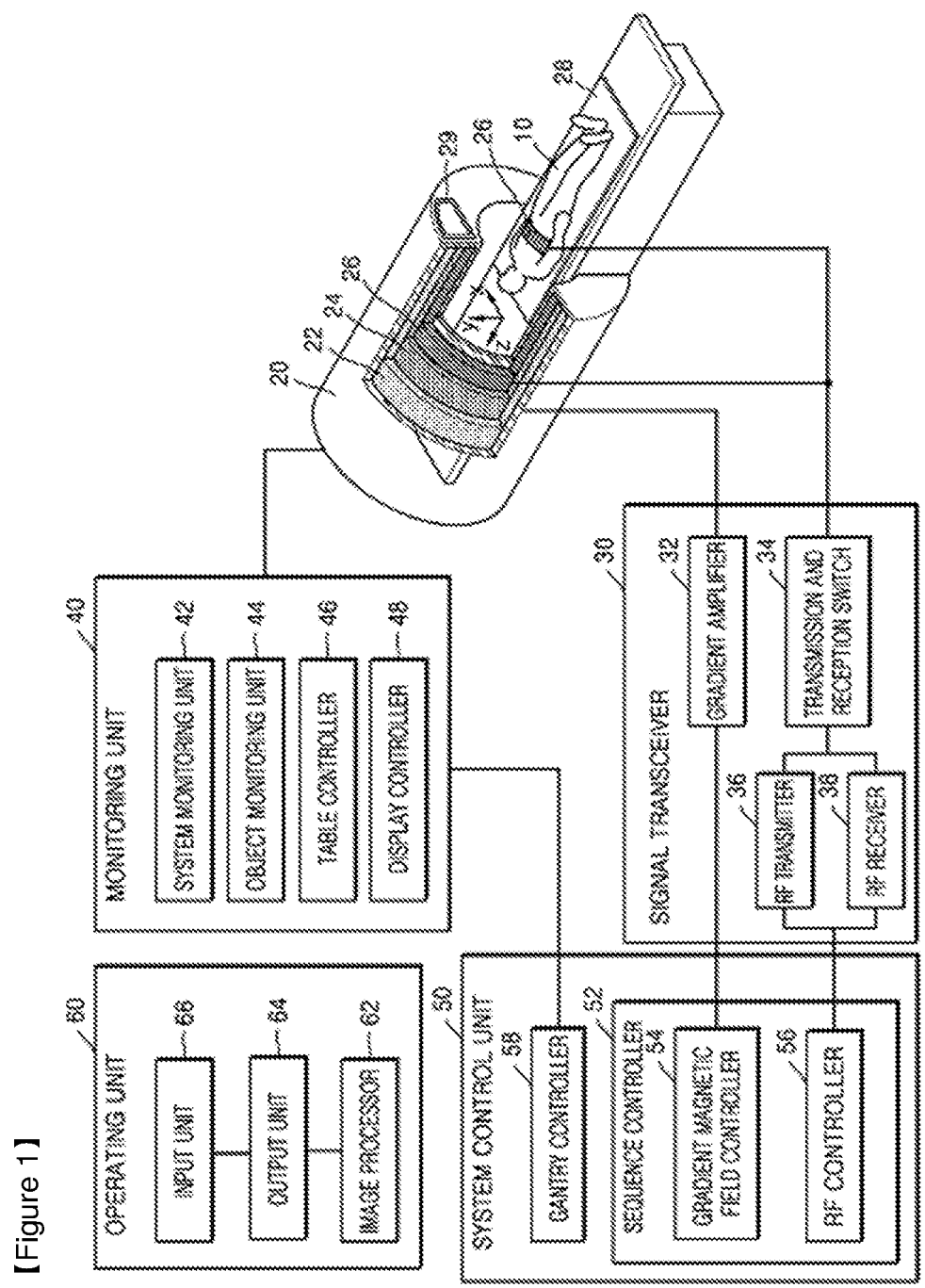
[Figure 1]

【Figure 2】
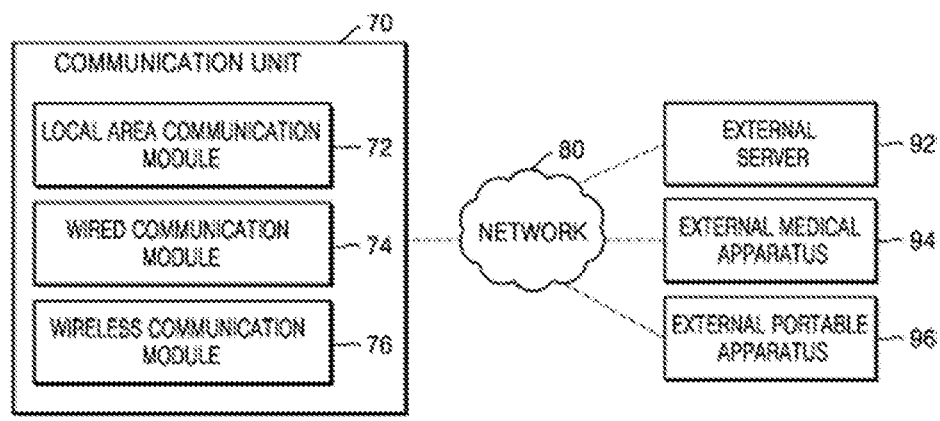
【Figure 3】
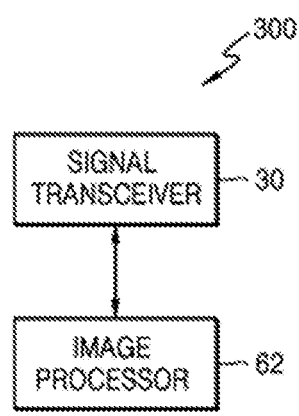

[Figure 4]
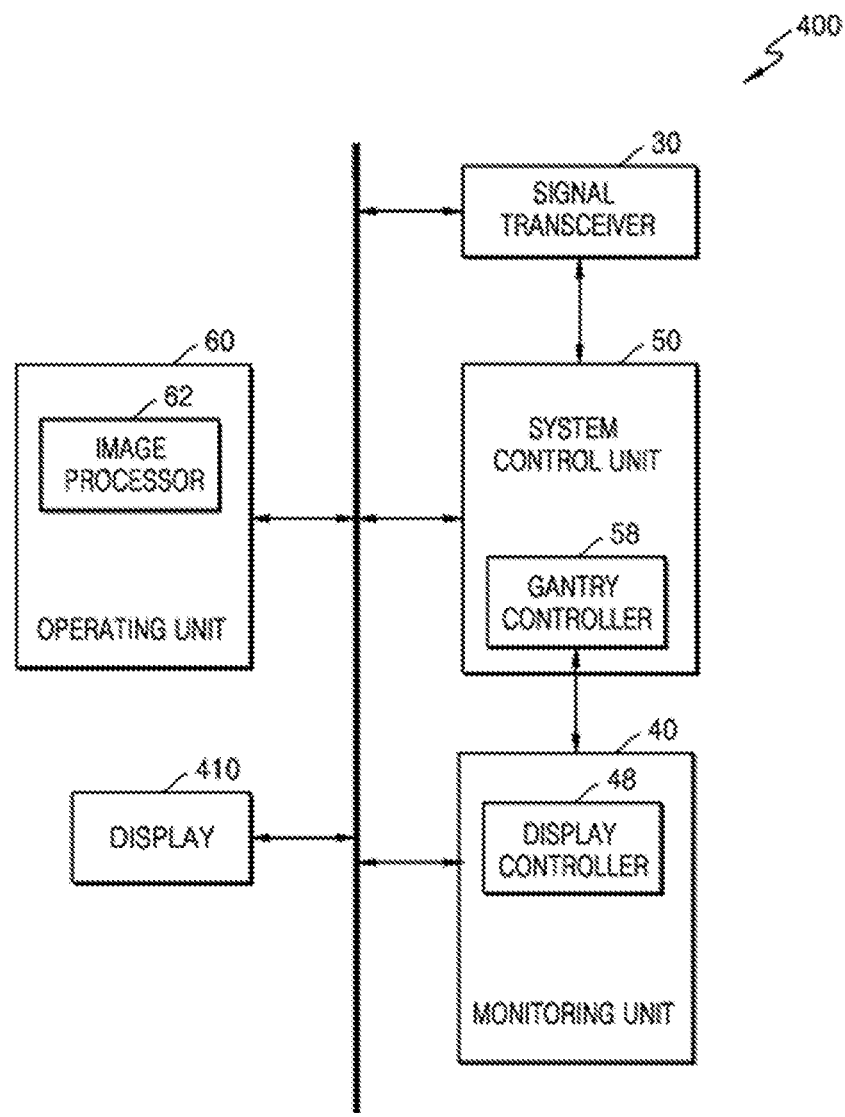

【Figure 5】
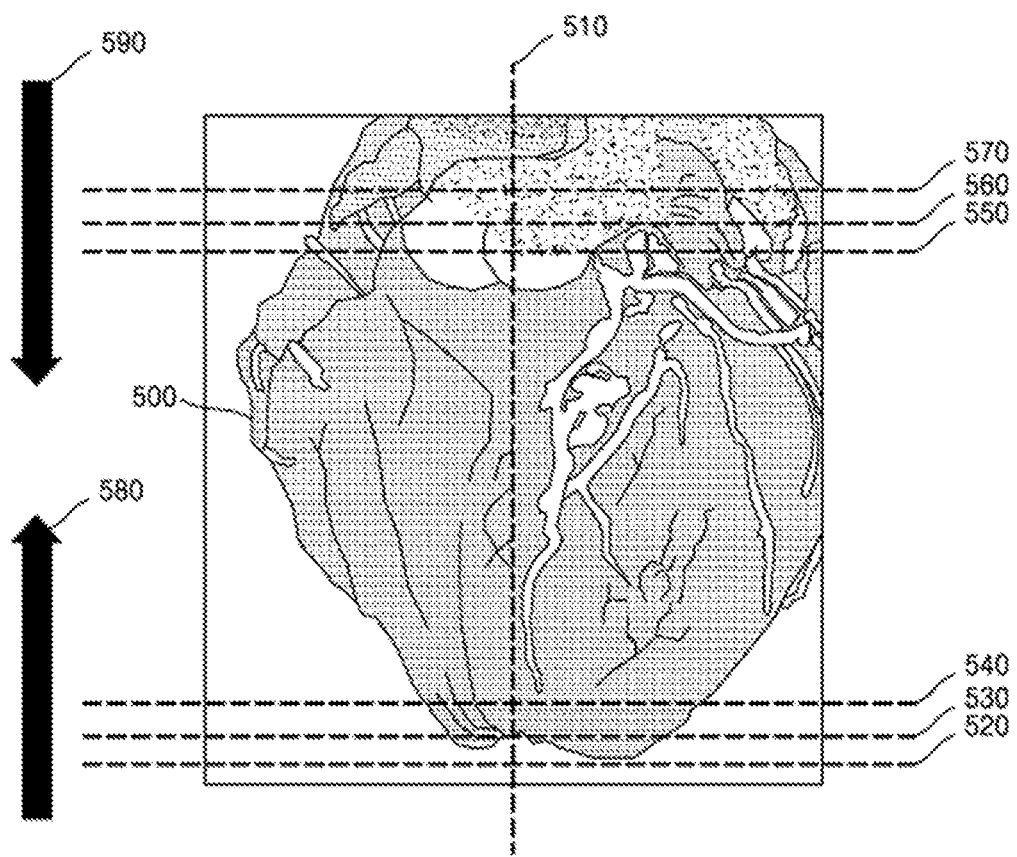

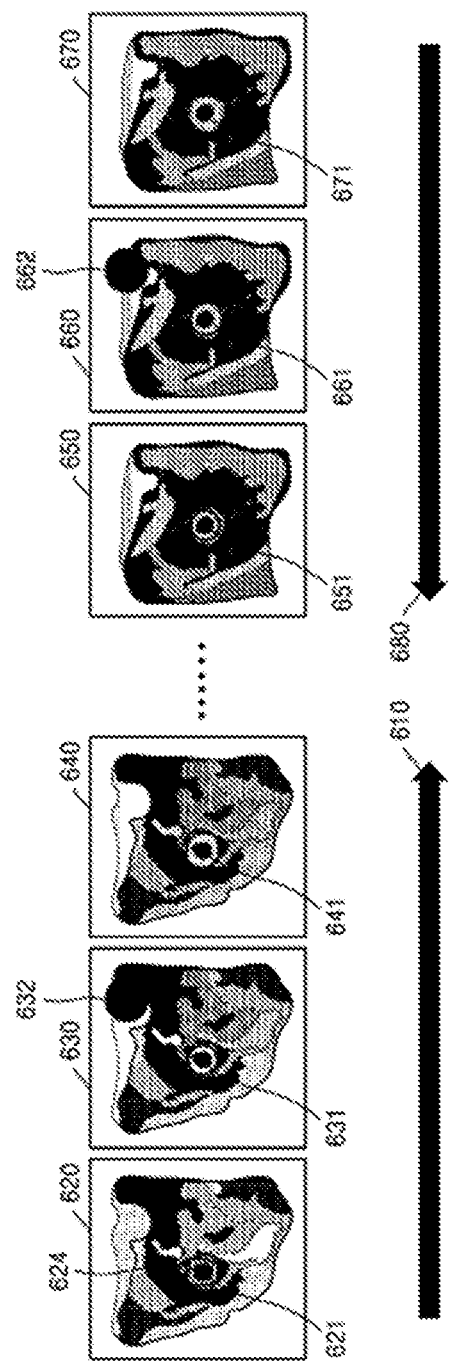
[Figure 6]

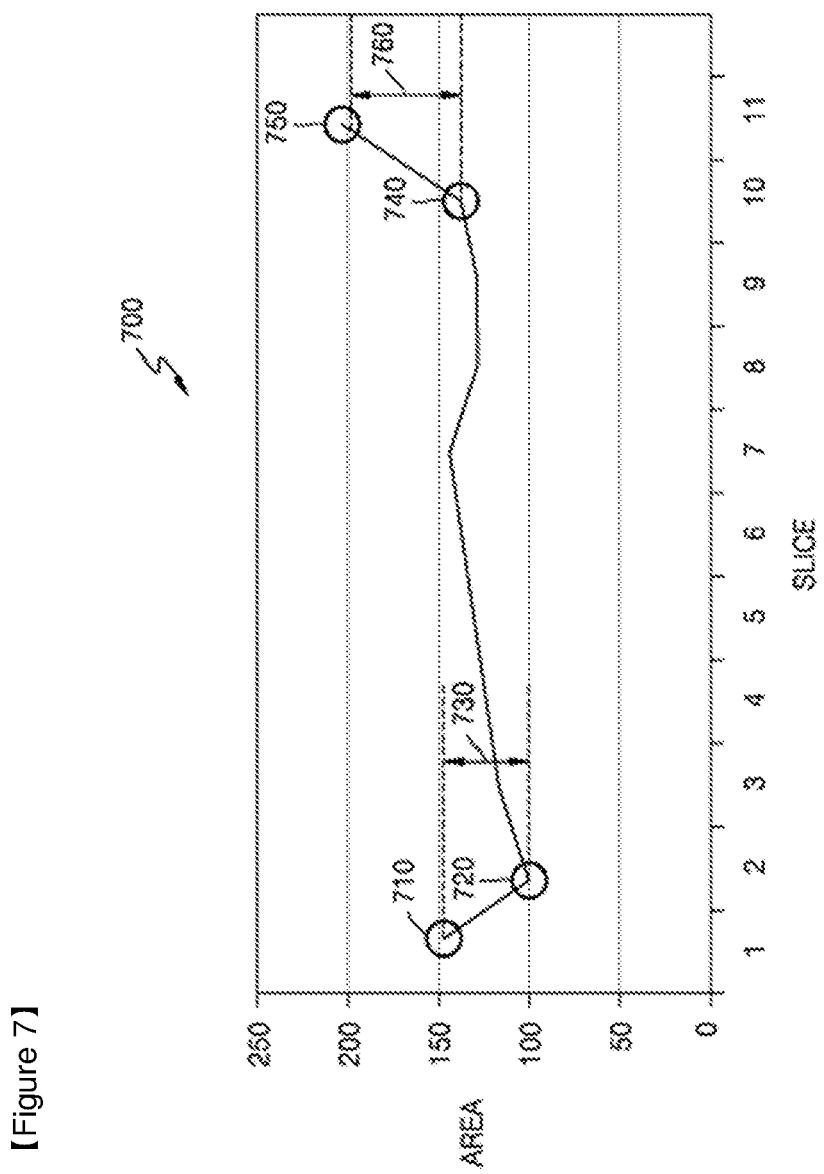
[Figure 7]

[Figure 8]

【Figure 10】
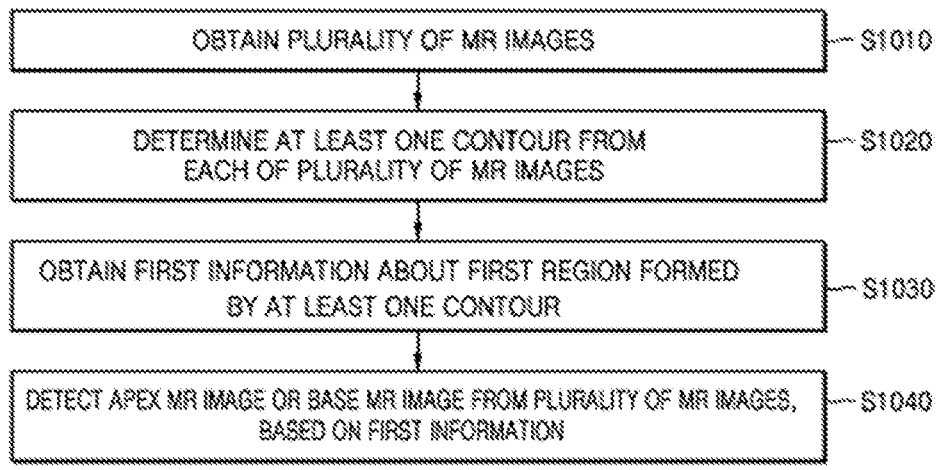
【Figure 11】
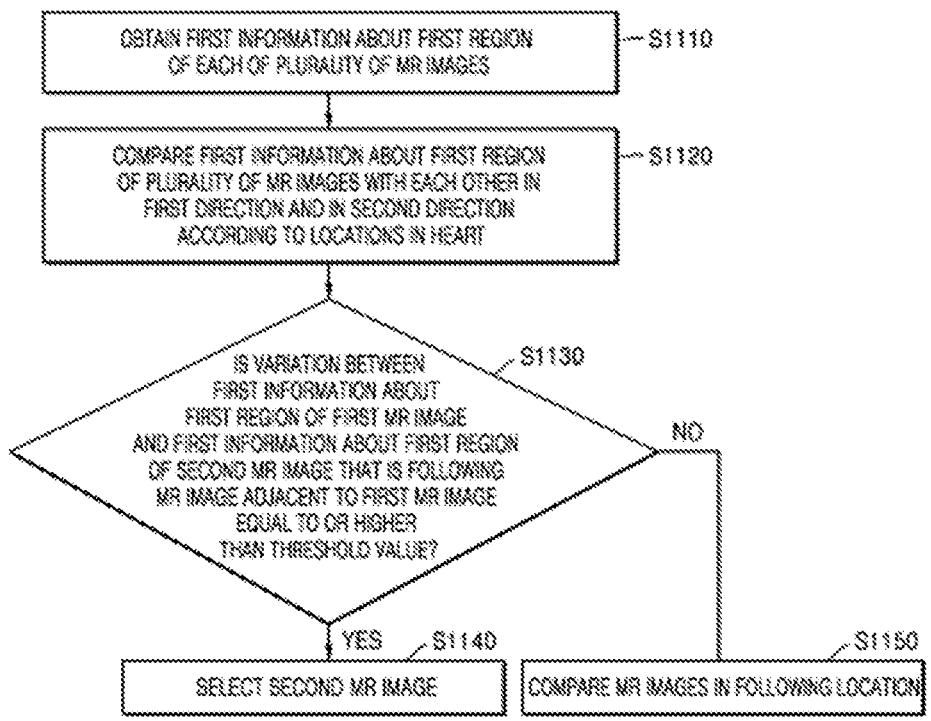

[Figure 12]
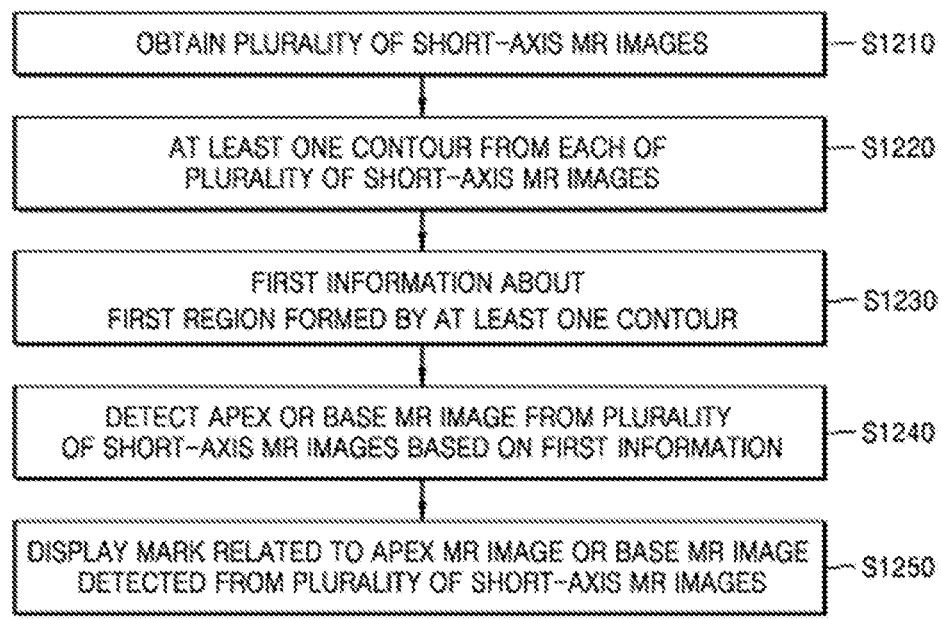

[Figure 13]
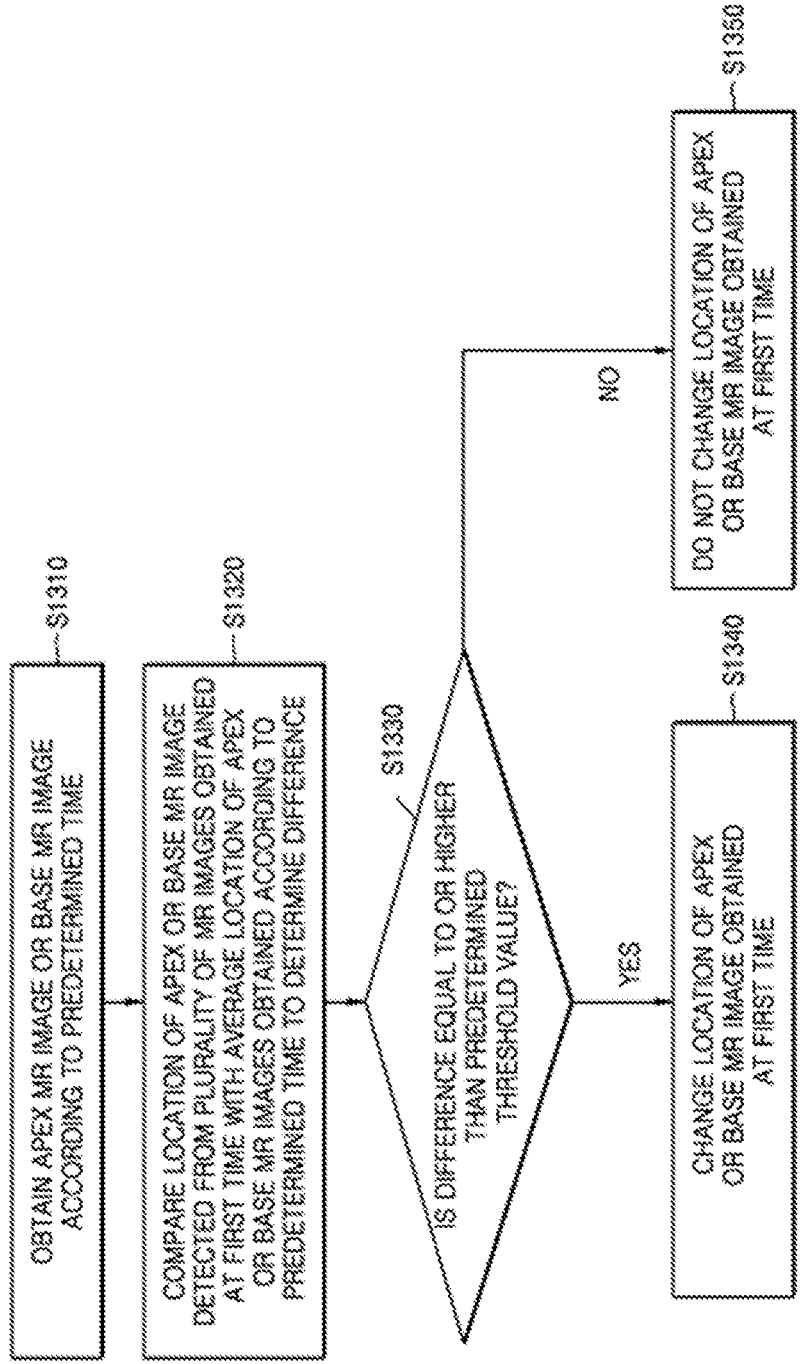

[Figure 14]
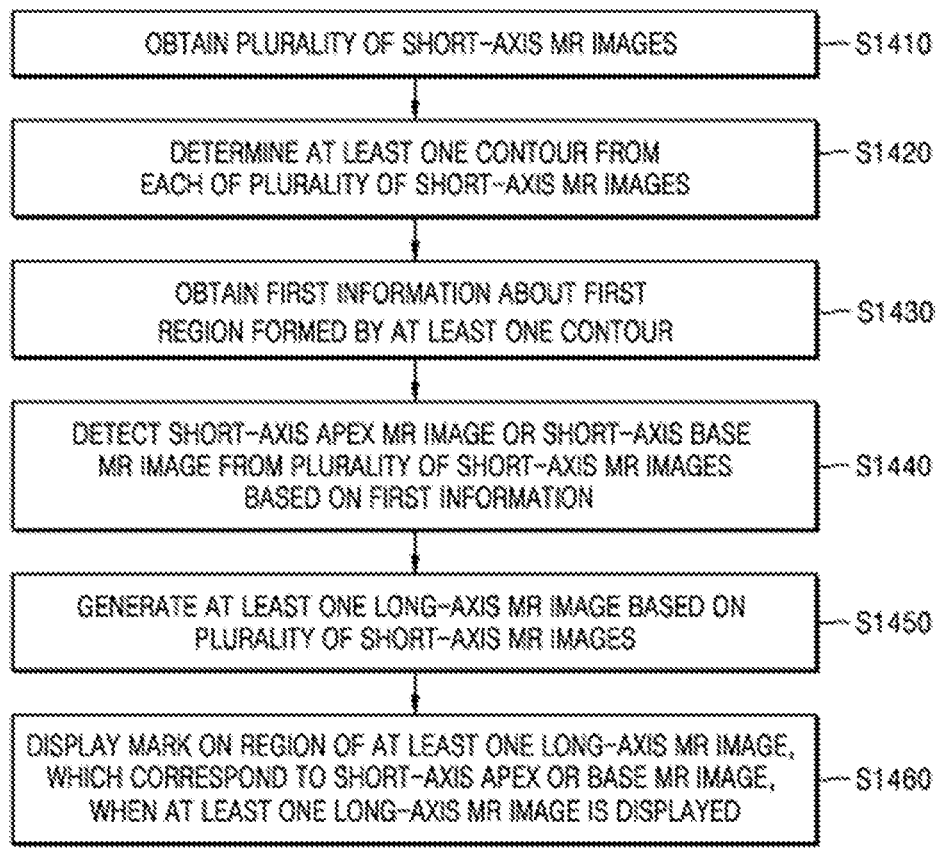

MAGNETIC RESONANCE IMAGE PROCESSING METHOD AND MAGNETIC RESONANCE IMAGE PROCESSING APPARATUS

TECHNICAL FIELD

One or more embodiments of the present invention relate to a magnetic resonance (MR) image processing apparatus and an MR image processing method, and more particularly, to an MR image processing apparatus and an MR image processing method, which automatically detect and process an apex MR image and a base MR image of the heart by using a short-axis MR image of the heart.

BACKGROUND ART

A magnetic resonance imaging (MRI) apparatus is an apparatus for photographing a subject by using a magnetic field and is widely used to accurately diagnose a disease since the MRI apparatus three-dimensionally shows not only bones but also disks, joints, nerves, ligaments, and the heart at any desired angle. Since the heart moves according to time, an MR image of the heart may be obtained and analyzed at certain times to determine a cardiac disorder.

In order to determine a cardiac disorder, a direction of the MRI apparatus is determined while capturing an MR image of the heart. The heart has a long-axis and a short-axis. The long-axis of the heart forms a line from a spleen to a right shoulder, and the short-axis of the heart is a line corresponding to an atrioventricular sulcus and forms a diagonal line close to a vertical line. A structure and movement of the heart may be three-dimensionally determined by obtaining MR images captured according to the short- and long-axes.

The heart includes a base and an apex, wherein the base is a region including an atrium and great arteries, and the apex is a region protruding below a stomach. During an MRI, the heart is photographed based on the base and the apex, and it is very important to determine locations of the base and the apex in the heart since information about the base and the apex is largely required while diagnosing a cardiac disorder.

DISCLOSURE

Technical Problem

One or more embodiments of the present invention include a magnetic resonance (MR) image processing method and an MR image processing apparatus, which quickly and accurately obtain an MR image of the heart, which shows at least one of an apex and a base.

In detail, one or more embodiments of the present invention include an MR image processing method and an MR image processing apparatus, which quickly and accurately obtain an MR image of a short-axis of the heart, which shows at least one of an apex and a base.

Technical Solution

According to one or more embodiments of the present invention, a magnetic resonance (MR) image processing method for processing an MR image of the heart, the MR image processing method includes: determining at least one contour from each of a plurality of MR images obtained by photographing the heart via magnetic resonance imaging (MRI); obtaining first information about a first region formed by the at least one contour; and detecting at least one of an apex MR image and a base MR image of the heart from among the plurality of MR images based on the first information.

Advantageous Effects

By using the present invention include a magnetic resonance (MR) image processing method and an MR image processing apparatus, it is provided to quickly and accurately obtain an MR image of the heart, which shows at least one of an apex and a base.

DESCRIPTION OF DRAWINGS

These and/or other aspects will become apparent and more readily appreciated from the following description of the embodiments, taken in conjunction with the accompanying drawings in which:

FIG. 1 is a block diagram of a general magnetic resonance imaging (MRI) system;

FIG. 2 is a block diagram of a communication unit according to an embodiment of the present invention;

FIG. 3 is a block diagram of an MR image processing apparatus according to an embodiment of the present invention;

FIG. 4 is a block diagram of an MR image processing apparatus according to another embodiment of the present invention;

FIG. 5 is a diagram of an MR image of the heart region;

FIG. 6 is a diagram of marks related to an apex or base MR image detected from a short-axis MR image;

FIG. 7 is a graph of a variation of first information about a first MR image;

FIG. 8 is a diagram of marks indicating an apex or a base from short-axis MR images obtained per predetermined time interval;

FIG. 9 is a diagram for describing changing of an apex or base MR image by comparing apex or base MR images detected from MR images obtained per predetermined time interval;

FIG. 10 is a flowchart of a method of detecting at least one of an apex MR image and a base MR image, according to an embodiment of the present invention;

FIG. 11 is a flowchart of a method of comparing a threshold value and a variation of first information about a first MR image so as to detect an apex MR image or a base MR image, according to an embodiment of the present invention;

FIG. 12 is a flowchart of a method of displaying a mark related to an apex or base MR image detected from a short-axis MR image, according to an embodiment of the present invention;

FIG. 13 is a flowchart of a method of changing a location of an apex or base MR image by comparing apex or base MR images detected from MR images obtained per predetermined time interval, according to an embodiment of the present invention; and FIG. 14 is a flowchart of a method of generating a long-axis MR image by using a short-axis MR image, and displaying a mark on a region of the long-axis MR image corresponding to a short-axis apex MR image or a short-axis base MR image detected from the short-axis MR image.

BEST MODE

According to one or more embodiments of the present invention, a magnetic resonance (MR) image processing method for processing an MR image of the heart, the MR image processing method includes: determining at least one contour from each of a plurality of MR images obtained by photographing the heart via magnetic resonance imaging (MRI); obtaining first information about a first region formed by the at least one contour; and detecting at least one of an apex MR image and a base MR image of the heart from among the plurality of MR images based on the first information.

The plurality of MR images may be obtained by performing an MRI along a short-axis of the heart, and may be MR images of a short-axis cross-section of the heart.

The obtaining of the first information may include: obtaining the first information about an area of the first region from the plurality of MR images; and when the plurality of MR images are arranged and compared according to locations in the heart based on the first information, selecting at least one second MR image wherein a variation of the areas of the first regions between a first MR image and the second MR image that is a following MR image adjacent to the first MR image from among the plurality of MR images is equal to or higher than a threshold value.

The detecting of the at least one of the apex MR image and the base MR image may include arranging the plurality of MR images according to locations in the heart and comparing the plurality of MR images in a first direction and a second direction opposite to the first direction of an arranged order to detect a second MR image that is initially selected from among the at least one second MR image in each of the first and second directions.

The MR image processing method may further include displaying at least one of the apex MR image and the base MR image.

The at least one of the apex MR image and the base MR image may be displayed by displaying a mark indicating an apex or a base.

The MR image processing method may further include: generating at least one long-axis MR image that is perpendicular to the short-axis, by using the plurality of MR images; and displaying at least one long-axis MR image based on the generated at least one long-axis MR image, wherein a mark may be displayed on a region of the displayed at least one long-axis MR image, which corresponds to the at least second MR image.

The plurality of MR images obtained by performing an MRI along the short-axis of the heart may include a plurality of MR images obtained by photographing a same location of the heart per predetermined time interval.

The detecting of the at least one of the apex MR image and the base MR image may include detecting at least one of the apex MR image and the base MR image per predetermined time interval, and the MR image processing method may further include, if a location of an apex MR image obtained at a first time is different from an average of locations of apex MR images obtained per predetermined time interval by a predetermined threshold value or higher, changing the location of the apex MR image obtained at the first time, and if a location of a base MR image obtained at a first time is different from an average of locations of base MR images obtained per predetermined time interval by a predetermined threshold value or higher, changing the location of the base MR image obtained at the first time.

The changing of the location of the apex or base MR image may include changing the apex MR image obtained at the first time to an average of locations of the apex in the plurality of MR images obtained by photographing the same location of the heart per predetermined time interval and changing the base MR image obtained at the first time to an average of locations of the base in the plurality of MR images obtained by photographing the same location of the heart per predetermined time interval.

According to one or more embodiments of the present invention, a magnetic resonance (MR) image processing apparatus for processing an MR image of the heart, the MR image processing apparatus includes: a signal transceiver that transmits or receives a signal to or from the heart; and an image processor that obtains a plurality of MR images of the heart by using the transmitted or received signal, determines at least one contour from each of the plurality of MR images; obtains first information about a first region formed by the at least one contour; and detects at least one of an apex MR image and a base MR image of the heart from among the plurality of MR images based on the first information.

The image processor may obtain the plurality of MR images by performing magnetic resonance imaging (MRI) along a short-axis of the heart, wherein the plurality of MR images may be MR images of a short-axis cross-section of the heart.

The image processor may obtain the first information based on an area of the first region from the plurality of MR images, and when the plurality of MR images are arranged and compared according to locations in the heart based on the first information, select at least one second MR image wherein a variation of the areas of the first regions between a first MR image and the second MR image that is a following MR image adjacent to the first MR image from among the plurality of MR images is equal to or higher than a threshold value.

When the plurality of MR images are arranged according to locations in the heart and the plurality of MR images are compared in a first direction and a second direction opposite to the first direction of an arranged order, the apex MR image or the base MR image may be a second MR image that is initially selected from among the at least one second MR image in each of the first and second directions.

The MR image processing apparatus may further include a display that displays the plurality of MR images including at least one of the apex MR image and the base MR image.

The display may display a mark indicating an apex or a base on at least one of the plurality of displayed MR images.

The image processor may generate at least one long-axis MR image that is perpendicular to the short-axis, by using the plurality of MR images; and the display may display the at least one long-axis MR image and display a mark on a region of the displayed at least one long-axis MR image, which corresponds to the at least second MR image.

The image processor may obtain the plurality of MR images obtained along the short-axis of the heart including a plurality of MR images obtained by photographing a same location of the heart per predetermined time interval.

The apex MR image or the base MR image may be detected per predetermined time interval, and if a location of an apex MR image obtained at a first time is different from an average of locations of apex MR images obtained per predetermined time interval by a predetermined threshold value or higher, the location of the apex MR image obtained at the first time may be changed, and if a location of a base MR image obtained at a first time is different from an average of locations of base MR images obtained per predetermined time interval by a predetermined threshold value or higher, the location of the base MR image obtained at the first time may be changed.

The changed location of the apex MR image may be an average of locations of the apex in the plurality of MR images obtained by photographing the same location of the heart per predetermined time interval, and the changed location of the base MR image may be an average of locations of the base in the plurality of MR images obtained by photographing the same location of the heart per predetermined time interval.

MODE FOR INVENTION

One or more embodiments of the present invention will now be described more fully with reference to the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Terms used herein will now be briefly described and then one or more embodiments of the present invention will be described in detail.

General terms widely used are selected while considering functions in one or more embodiments of the present invention for terms used herein, but the terms used herein may differ according to intentions of one of ordinary skill in the art, precedents, or emergence of new technologies. Also, in some cases, an applicant arbitrarily selects a term, and in this case, the meaning of the term will be described in detail herein. Accordingly, the terms shall be defined based on the meanings and details throughout the specification, rather than the simple names of the terms.

When something 「includes」 a component, another component may be further included unless specified otherwise. The term 「unit」 used in the present specification refers to a software component, or a hardware component such as FPGA or ASIC, and performs a certain function. However, the 「unit」 is not limited to software or hardware. The 「unit」 may be configured in an addressable storage medium and may be configured to be executed by one or more processors. Hence, the 「unit≈ includes elements such as software elements, object-oriented software elements, class elements, and task elements, and processes, functions, attributes, procedures, sub-routines, segments of program codes, drivers, firmware, micro-codes, circuits, data, databases, data structures, tables, arrays, and variables. The functions provided in the elements and the units may be combined into a fewer number of elements and units or may be divided into a larger number of elements and units.

As used herein, the term "and/or" includes any and all combinations of one or more of the associated listed items. Expressions such as 「at least one of, 」 when preceding a list of elements, modify the entire list of elements and do not modify the individual elements of the list.

While describing one or more embodiments of the present invention, descriptions about drawings that are not related to the one or more embodiments of the present invention are omitted.

In the present specification, an 「image」 may refer to multi-dimensional data composed of discrete image elements (e.g., pixels in a two-dimensional image and voxels in a three-dimensional image). For example, an image may include a medical image of an object acquired by X-rays, computed tomography (CT), magnetic resonance imaging (MRI), ultrasonic waves, or other medical image photographing apparatuses.

Furthermore, in the present specification, an 「object」 may include a person or an animal, or a part of a person or an animal. For example, the object may include the liver, the heart, the womb, the brain, a breast, the abdomen, or a blood vessel. Furthermore, the 「object」 may include a phantom. The phantom means a material having a volume that is approximately the intensity and effective atomic number of a living thing, and may include a sphere phantom having a property similar to a human body.

Furthermore, in the present specification, a 「user」 refers to a medical professional, such as a doctor, a nurse, a medical laboratory technologist, and an engineer who repairs a medical apparatus, but the user is not limited thereto.

Furthermore, in the present specification, an 「MRI」 refers to an image of an object obtained by using the nuclear magnetic resonance principle.

Furthermore, in the present specification, 「pulse sequence」 refers to continuity of signals repeatedly applied by an MRI apparatus. A pulse sequence may include a time parameter of a radio frequency (RF) pulse, for example, repetition time (TR) or echo time (TE).

Furthermore, in the present specification, a 「pulse sequence mimetic diagram」 shows an order of events that occur in an MRI apparatus. For example, a pulse sequence mimetic diagram may be a diagram showing an RF pulse, a gradient magnetic field, or an MR signal according to time.

An MRI system is an apparatus for acquiring a sectional image of a part of an object by expressing, in a contrast comparison, the strength of an MR signal with respect to a radio frequency (RF) signal generated in a magnetic field having a specific strength. For example, if an RF signal that resonates only a specific atomic nucleus (for example, a hydrogen atomic nucleus) is irradiated for an instant onto the object that is placed in a strong magnetic field and then such irradiation stops, an MR signal is emitted from the specific atomic nucleus, and thus the MRI system may receive the MR signal and acquire an MR image. The MR signal denotes an RF signal emitted from the object. An intensity of the MR signal may be determined according to the density of a predetermined atom (for example, hydrogen) of the object, a relaxation time T1, a relaxation time T2, and blood flow.

MRI systems have different characteristics from those of other imaging apparatuses. Unlike imaging apparatuses such as computed tomography (CT) apparatuses that acquire images depending upon a direction of detection hardware, MRI systems may acquire two-dimensional (2D) images or three-dimensional (3D) volume images that are oriented toward a selected point. MRI systems do not expose objects and examinees to radiation, unlike CT apparatuses, X-ray apparatuses, position emission tomography (PET) apparatuses, and single photon emission CT (SPECT) apparatuses, may acquire images having high soft tissue contrast, and may acquire neurological images, intravascular images, musculoskeletal images, and oncologic images that are important to precisely describe abnormal tissue.

FIG. 1 is a block diagram of a general MRI system. Referring to FIG. 1, the general MRI system may include a gantry 20, a signal transceiver 30, a monitoring unit 40, a system control unit 50, and an operating unit 60.

The gantry 20 blocks electromagnetic waves generated by a main magnet 22, a gradient coil 24, and an RF coil 26 from being externally emitted. A magnetostatic field and a gradient magnetic field are formed at a bore in the gantry 20, and an RF signal is irradiated towards an object 10.

The main magnet 22, the gradient coil 24, and the RF coil 26 may be arranged in a predetermined direction of the gantry 20. The predetermined direction may be a coaxial cylinder direction. The object 10 may be disposed on a table 28 that is capable of being inserted into a cylinder along a horizontal axis of the cylinder.

The main magnet 22 generates a magnetostatic field or a static magnetic field for aligning magnetic dipole moments of atomic nuclei of the object 10 in a constant direction. A precise and accurate MR image of the object 10 may be obtained when a magnetic field generated by the main magnet 22 is strong and uniform.

The gradient coil 24 includes X, Y, and Z coils for generating gradient magnetic fields in X-, Y-, and Z-axis directions crossing each other at right angles. The gradient coil 24 may provide location information of each region of the object 10 by differently inducing resonance frequencies according to the regions of the object 10.

The RF coil 26 may irradiate an RF signal to a patient and receive an MR signal emitted from the object 10. In detail, the RF coil 26 may transmit an RF signal at a same frequency as precessional motion to the patient towards atomic nuclei in precessional motion, stop transmitting the RF signal, and then receive an MR signal emitted from the object 10.

For example, an atomic nucleus transits from a low energy state to a high energy state, the RF coil 26 may generate and apply an electromagnetic wave signal having an RF corresponding to a type of the atomic nucleus, for example, an RF signal, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus, to which the electromagnetic waves were applied, transits from the high energy state to the low energy state, thereby emitting electromagnetic waves having a Larmor frequency. In other words, when the electromagnetic wave signal is no longer applied to the atomic nucleus, an energy level of the atomic nucleus is changed from a high energy level to a low energy level, and thus the atomic nucleus may emit electromagnetic waves having a Larmor frequency. The RF coil 26 may receive electromagnetic wave signals from atomic nuclei of the object 10.

The RF coil 26 may be realized as one RF transmitting and receiving coil having both a function of generating electromagnetic waves having a wireless frequency corresponding to a type of an atomic nucleus and a function of receiving electromagnetic waves emitted from an atomic nucleus. Alternatively, the RF coil 26 may be realized as a transmission RF coil having a function of generating electromagnetic waves having a wireless frequency corresponding to a type of an atomic nucleus, and a reception RF coil having a function of receiving electromagnetic waves emitted from an atomic nucleus.

The RF coil 26 may be detachably fixed to the gantry 20. When the RF coil 26 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly and may also perform dual tune communication according to a communication frequency band.

The RF coil 26 may be a birdcage coil, a surface coil, or a transverse electromagnetic (TEM) coil according to structures of a coil.

The RF coil 26 may be a transmission exclusive coil, a reception exclusive coil, or a transmission and reception coil according to methods of transmitting and receiving an RF signal.

The RF coil 26 may be an RF coil in any one of various channels, such as 16 channels, 32 channels, 72 channels, and 144 channels.

The gantry 20 may further include a display 29 disposed outside the gantry 20 and a display (not shown) disposed inside the gantry 20. The gantry 20 may provide predetermined information to the user or the object 10 through the display 29 and the display respectively disposed outside and inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 may include a gradient amplifier 32, a transmission and reception switch 34, an RF transmitter 36, and an RF receiver 38.

The gradient amplifier 32 drives the gradient coil 24 in the gantry 20 and may supply a pulse signal for generating a gradient magnetic field to the gradient coil 24 according to control of a gradient magnetic field controller 54. By controlling the pulse signal supplied from the gradient amplifier 32 to the gradient coil 24, gradient magnetic fields in X-, Y-, and Z-axis directions may be composed.

The RF transmitter 36 and the RF receiver 38 may drive the RF coil 26. The RF transmitter 36 may supply an RF pulse at a Larmor frequency to the RF coil 26, and the RF receiver 38 may receive an MR signal received by the RF coil 26.

The transmission and reception switch 34 may adjust transmitting and receiving directions of the RF signal and the MR signal. For example, the RF signal may be irradiated to the object 10 through the RF coil 26 during a transmission mode, and the MR signal may be received by the object 10 through the RF coil 26 during a reception mode. The transmission and reception switch 34 may be controlled by a control signal from an RF controller 56.

The monitoring unit 40 may monitor or control the gantry 20 or devices mounted on the gantry 20. The monitoring unit 40 may include a system monitoring unit 42, an object monitoring unit 44, a table controller 46, and a display controller 48.

The system monitoring unit 42 may monitor and control a state of a magnetostatic field, a state of a gradient magnetic field, a state of an RF signal, a state of an RF coil, a state of a table, a state of a device measuring body information of an object, a power supply state, a state of a thermal exchanger, and a state of a compressor.

The object monitoring unit 44 monitors a state of the object 10. In detail, the object monitoring unit 44 may include a camera for observing the movement or position of the object 10, a respiration measurer for measuring the respiration of the object 10, an ECG measurer for measuring ECG of the object 10, or a temperature measurer for measuring a temperature of the object 10.

The table controller 46 controls movement of the table 28 where the object 10 is positioned. The table controller 46 may control the movement of the table 28 according to sequence control of a sequence controller 52. For example, during moving imaging of the object 10, the table controller 46 may continuously or discontinuously move the table 28 according to the sequence control of the sequence controller 52, and thus the object 10 may be photographed in a larger field of view (FOV) than that of the gantry 20.

The display controller 48 controls the display 29 and the display respectively outside and inside the gantry 20. In detail, the display controller 48 may turn on or off the display 29 and the display outside and inside the gantry 20 and may control a screen to be output on the display 29 and the display. Also, when a speaker is located inside or outside the gantry 20, the display controller 48 may turn on or off the speaker or control the speaker to output sound.

The system control unit 50 may include the sequence controller 52 for controlling a sequence of signals formed in the gantry 20, and a gantry controller 58 for controlling the gantry 20 and devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating unit 60. Here, the pulse sequence includes all information required to control the gradient amplifier 32, the RF transmitter 36, the RF receiver 38, and the transmission and reception switch 34, for example, may include information about the strength, an application time, and an application timing of a pulse signal applied to the gradient coil 24.

The operating unit 60 requests the system control unit 50 to transmit pulse sequence information while controlling an overall operation of the MRI system.

The operating unit 60 may include an image processor 62 for processing an MR signal received from the RF receiver 38, an output unit 64, and an input unit 66.

The image processor 62 processes an MR signal received from the RF receiver 38 so as to generate MR image data of the object 10.

The image processor 62 performs any one of various signal processes, such as amplification, frequency transformation, phase detection, low frequency amplification, and filtering, on an MR signal received by the RF receiver 38.

The image processor 62 may arrange digital data in a k space (for example, also referred to as a Fourier space or frequency space) of a memory and rearrange the digital data into image data via 2D or 3D Fourier transformation.

The image processor 62 may perform a composition process or difference calculation process on image data if required. The composition process may include an addition process on a pixel or a maximum intensity projection (MIP) process. The image processor 62 may store not only rearranged image data but also image data on which a composition process or difference calculation process is performed, in a memory (not shown) or an external server.

Signal processes applied to MR signals by the image processor 62 may be performed in parallel. For example, a signal process may be performed on a plurality of MR signals received by a multi-channel RF coil in parallel so as to rearrange the plurality of MR signals as image data.

The output unit 64 may output image data generated or rearranged by the image processor 62 to the user. Also, the output unit 64 may output information required for the user to manipulate the MRI system, such as a user interface (UI), user information, or object information. The output unit 64 may include a speaker, a printer, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a PFD display, a 3-dimensional (3D) display, or a transparent display, or any one of various output devices that are well known to one of ordinary skill in the art.

The user may input object information, parameter information, scan conditions, a pulse sequence, or information about image composition or difference calculation by using the input unit 66. The input unit 66 may include a keyboard, a mouse, a track ball, a voice recognizer, a gesture recognizer, or a touch screen, or may include any one of other various input devices that are well known to one of ordinary skill in the art.

The signal transceiver 30, the monitoring unit 40, the system control unit 50, and the operating unit 60 are separate components in FIG. 1. However, it is obvious to one of ordinary skill in the art that functions of the signal transceiver 30, the monitoring unit 40, the system control unit 50, and the operating unit 60 may be performed by another component. For example, the image processor 62 converts an MR signal received by the RF receiver 38 into a digital signal, but such a conversion to a digital signal may be directly performed by the RF receiver 38 or the RF coil 26.

The gantry 20, the RF coil 26, the signal transceiver 30, the monitoring unit 40, the system control unit 50, and the operating unit 60 may be connected to each other via wires or wirelessly, and when they are connected wirelessly, the MRI system may further include an apparatus (not shown) for synchronizing clocks therebetween. Communication between the gantry 20, the RF coil 26, the signal transceiver 30, the monitoring unit 40, the system control unit 50, and the operating unit 60 may be performed by using a high-speed digital interface, such as low voltage differential signaling (LVDS), asynchronous serial communication, such as universal asynchronous receiver transmitter (UART), a low-delay network protocol, such as an error synchronous serial communication or controller area network (CAN), or optical communication, or any other communication method that is well known to one of ordinary skill in the art.

FIG. 2 is a block diagram of a communication unit 70 according to an embodiment of the present invention.

The communication unit 70 may be connected to at least one of the gantry 20, the signal transceiver 30, the monitoring unit 40, the system control unit 50, and the operating unit 60 of FIG. 1.

The communication unit 70 may transmit or receive data to or from a hospital server or another medical apparatus in a hospital connected through a picture archiving and communication system (PACS) and perform data communication according to the digital imaging and communications in medicine (DICOM) standard.

As shown in FIG. 2, the communication unit 70 may be connected to a network 80 via wires or wirelessly to communicate with an external server 92, an external medical apparatus 94, or an external portable apparatus 96.

In detail, the communication unit 70 may transmit or receive data related to the diagnosis of an object through the network 80 and may also transmit or receive a medical image captured by the external medical apparatus 94, such as a CT, an MRI, or an X-ray apparatus. In addition, the communication unit 70 may receive a diagnosis history or a treatment schedule of the object from the external server 92 to diagnose the object. The communication unit 70 may perform data communication not only with the external server 92 or external medical apparatus 94 in a hospital, but also with the external portable apparatus 96, such as a mobile phone, a personal digital assistant (PDA), or a laptop of a doctor or customer.

Also, the communication unit 70 may transmit information about a malfunction of the MRI system or about a medical image quality to a user through the network 80 and receive feedback from the user.

The communication unit 70 may include at least one component enabling communication with an external apparatus, for example, a local area communication module 72, a wired communication module 74, and a wireless communication module 76.

The local area communication module 72 is a module for performing local area communication with a device within a predetermined distance. Examples of local area communication technology include a wireless local area network (LAN), Wi-Fi, Bluetooth, ZigBee, Wi-Fi direct (WFD), ultra wideband (UWB), infrared data association (IrDA), Bluetooth low energy (BLE), and near field communication (NFC), but are not limited thereto.

The wired communication module 74 is a module for performing communication by using an electric signal or an optical signal. Examples of wired communication technology include wired communication technologies using a pair cable, a coaxial cable, and an optical fiber cable, and other well-known wired communication technologies.

The wireless communication module 76 transmits or receives a wireless signal to or from at least one of a base station, an external apparatus, and a server in a mobile communication network. Here, the wireless signal may include data in any one of various formats according to transmitting and receiving a voice call signal, a video call signal, and a text/multimedia message.

FIG. 3 is a block diagram of an MR image processing apparatus 300 according to an embodiment of the present invention.

Referring to FIG. 3, the MR image processing apparatus 300 according to an embodiment includes the signal receiver 30 and the image processor 62. The signal transceiver 30 and the image processor 62 of FIG. 3 may correspond to the signal transceiver 30 and the image processor 62 of FIG. 1, and thus repeated descriptions thereof are not provided again. Also, the MR image processing apparatus 300 may be the external server 92, the external medical apparatus 94, or the external portable apparatus 96 of FIG. 2 that transmits or receives a predetermined signal to or from the general MRI system of FIG. 1.

The signal transceiver 30 transmits or receives a signal to or from the heart. Here, the transmitted or received signal may be an RF signal that is transmitted or received through the RF transmitter 36 and the RF receiver 38, or may be raw data generated by using the RF signal. Here, the raw data may be k space data obtained by disposing the RF signal in a k space. Hereinafter, it is assumed that the signal transmitted or received by the signal transceiver 30 is an MR signal or an RF signal.

In detail, the signal transceiver 30 includes the RF receiver 38 shown in FIG. 1, and may directly receive an MR signal detected by the RF coil 26 of FIG. 1. Also, the signal transceiver 30 may be connected to the RF receiver 38 of FIG. 1 and may receive an MR signal from the RF receiver 38. An RF signal received by the signal transceiver 30 may be one or both of a short-axis MR signal and a long-axis MR signal of the heart of the object 10.

The image processor 62 generates an MR image based on the RF signal received by the signal transceiver 30. The image processor 62 obtains a plurality of MR images of the heart by using transmitted or received signals and determines at least one contour from each of the plurality of MR images. For example, if the object 10 is the heart, a contour may be a wall of the heart, and in detail, may be a contour indicated by a surface forming a left ventricle.

Also, the image processor 62 obtains first information about a first region formed by the at least one contour and detects at least one of an apex MR image and a base MR image of the heart from the plurality of MR images, based on the first information. Here, the first information may be about an area, a center point, an average brightness, a standard deviation of brightness, a shape, or a radius of the first area.

In detail, when the object 10 is put into a magnetic field and the signal transceiver 30 instantaneously irradiates, to the object 10, an RF signal that resonates only a certain atomic nucleus, an MR signal is emitted from the certain atomic nucleus, i.e., an RF signal is emitted from the object 10. When the signal transceiver 30 receives such an RF signal, the image processor 62 generates an MR image based on the RF signal.

The MR image processing apparatus 300 according to an embodiment may determine at least one contour from each of a plurality of MR images obtained by photographing the heart via an MRI, obtain first information about a first region formed by the at least one contour, and detect at least one of an apex MR image and a base MR image of the heart from the plurality of MR images based on the first information.

FIG. 4 is a block diagram of an MR image processing apparatus 400 according to another embodiment of the present invention. Compared to the MR image processing apparatus 300 of FIG. 3, the MR image processing apparatus 400 of FIG. 4 may further include the system control unit 50, the display controller 48, and a display 410. Also, the image processor 62 may be included in the operating unit 60.

Referring to FIG. 4, in the MR image processing apparatus 400, the system control unit 50 may control the image processor 62 that may be included in the operating unit 60 to generate an MR image, based on an MR signal received by the signal transceiver 30. The gantry controller 58 that may be included in the system control unit 50 may control the display controller 48 for controlling the display 410 disposed inside or outside the gantry 20.

The display controller 48 controls the display 410 to display a predetermined screen.

The display 410 may display the predetermined screen so that a user or a patient visually recognizes a predetermined image or information. The display 410 may correspond to the display 29 of FIG. 1 and may be configured separately from the general MRI system of FIG. 1.

The display 410 may display an MR image generated by the image processor 62 based on an MR signal received by the signal transceiver 30. According to an embodiment of the present invention, if the image processor 62 generates a short-axis MR image of the heart of the object 10, the display 410 may display the short-axis MR image, and if the image processor 62 generates a short-axis MR image and a long-axis MR image, the display 410 may display the short-axis MR image and the long-axis MR image.

The image processor 62 may generate a mark for distinguishing an MR image to be detected from another MR image while generating the MR image, and the display controller 48 may control the display 410 to display the generated MR image and the mark for distinguishing the MR image to be detected from the other MR image. According to an embodiment of the present invention, the MR image to be detected may be an apex or base MR image, and the mark may be identically or differently displayed according to an apex or a base. The mark may be automatically displayed, and the displayed mark may be manually changed by a user later to a mark of the other MR image.

FIG. 5 is a diagram of an MR image of the heart region.

Referring to FIG. 5, an MR image is generated by photographing the heart 500 that is a target object via an MRI. In detail, the image processor 62 may obtain a plurality of MR images by performing an MRI on the heart 500 according to a short-axis. In detail, the plurality of MR images may be cross-sectional MR images in the short-axis of the heart 500.

In order to determine a cardiac disorder, MR images in various axes of the heart 500 may be obtained and analyzed, and in order to generate MR images of only the heart 500, locations of an apex and a base of the heart 500 may be determined. Moreover, it is very important to obtain a short-axis image of the heart 500 when diagnosing a cardiac disorder. Accordingly, the image processor 62 may perform MRI by using slices 520 through 570 indicating axial cross sections corresponding to surfaces perpendicular to a long-axis 510 of the heart 500, and generate short-axis MR images corresponding to the slices 520 through 570. The generated short-axis MR images may be arranged and compared according to locations in the heart 500, wherein an arrangement order may be in a first direction 580 or a second direction 590 parallel to a short-axis 510.

FIG. 6 is a diagram of marks related to an apex or base MR image detected from a short-axis MR image.

An MR image processing apparatus according to an embodiment of the present invention may include a display that displays a plurality of MR images including at least one of an apex MR image and a base MR image, wherein the display may display a mark related to at least one of the apex MR image and the base MR image. The mark may be identically or differently displayed according to an apex or a base, wherein the mark may be automatically displayed and the displayed mark may be manually changed by a user later to a mark related to another MR image.

Referring to FIG. 6, MR images 620 through 670 are short-axis MR images of the heart of the object 10 and respectively correspond to the slices 520 through 570. For example, the MR image 620 may be a short-axis MR image indicating an axial cross-section corresponding to the slice 520, and the MR image 630 may be a short-axis MR image indicating an axial cross-section corresponding to the slice 530. Each short-axis MR image may include a first region formed by at least one contour. For example, a first region 621 may be formed by a contour 624. For example, if the object 10 is the heart, a contour may be formed by a heart wall, and in detail, may include a contour indicated by a surface forming a left ventricle. In FIG. 6, the contour 624 is a contour indicated by a surface forming a left ventricle.

The image processor 62 compares MR images adjacent to each other in a first direction 610 and in a second direction 680 with respect to the short-axis MR images. The first direction 610 of FIG. 6 may be the first direction 580 of FIG. 5, and the second direction 680 of FIG. 6 may be the second direction 590 of FIG. 5.

In detail, the image processor 62 may obtain first information based on an area of a first area in each of a plurality of MR images, and when the plurality of MR images are arranged and compared according to locations in the heart based on the first information, select at least one second MR image wherein a variation of the areas of the first regions between a first MR image and a second MR image that is a following MR image adjacent to the first MR image from among the plurality of MR images is equal to or higher than a threshold value. Here, the first information may be about an area, a center point, an average brightness, a standard deviation of brightness, a shape, or a radius of the first region, and the threshold value may be set based on a type of the first information to select an MR image to be detected. According to an embodiment of the present invention, the first information may be the area of the first region, and hereinafter, it is assumed that the first information is about the area of the first region.

Referring to FIG. 6, the image processor 62 may, while comparing the MR images 620 through 670 in the first direction 610, select the MR image 630 as a second MR image since a variation of an area of the first region 621 of the MR image 620 as a first MR image and an area of a first region 631 of the MR image 630 adjacent to the MR image 620 is higher than a predetermined threshold value. Then, the image processor 62 may, while comparing the MR images 620 through 670 in the second direction 680, select the MR image 660 as a second MR image since a variation of an area of a first region 671 of the MR image 670 as a first MR image and an area of a first region 661 of the MR image 660 adjacent to the MR image 670 is higher than the predetermined threshold value. The selected MR images 630 and 660 are some of the at least one second MR image, and moreover, since the MR images 630 and 660 are initially selected from among the at least one second MR image, the MR images 630 and 660 may be detected as apex or base MR images. The MR images 630 and 660 may be displayed, and at the same time, marks 632 and 662 for distinguishing the MR images 630 and 660 from other MR images 620, 640, 650, and 670 may be respectively displayed on the MR images 630 and 660.

A variation of areas in contours included in first regions will now be described in detail with reference to FIG. 7.

FIG. 7 is a graph 700 of a variation of first information about a first MR image.

Referring to FIG. 7, the graph 700 indicates a relationship between a slice and an area of a first region, i.e., first information about the first region. An X-axis denotes slices, wherein, from among the slices 520 through 570 of FIG. 5, the slice 520 at the bottom may be a first slice, and the slice 570 at the top may be an 11th slice. A Y-axis denotes an area of a first region.

Referring to FIGS. 6 and 7, the area of the first region 621 included in the MR image 620 corresponds to an area 710, and the area of the first region 631 included in the MR image 630 corresponds to an area 720. Also, the area of the first region 661 included in the MR image 660 corresponds to an area 740, and the area of the first region 671 included in the MR image 670 corresponds to an area 750.

Also, a plot in the graph 700 is formed by linearly connecting locations corresponding to the areas 710, 720, 740, and 750 according to the slices. Here, the area 710 of the first region of the first slice from among the slices may be 150, the area 720 of the first region of the second slice may be 100, the area 740 of the first region of the 10th slice may be 140, and the area 750 of the first region of the 11th slice may be 200. If a predetermined threshold value to be compared with the variation of the first information about the first region is set to be 50 and comparison is performed from the first slice to the 11th slice, a variation 730 of the areas of the first regions of the first slice that is a first MR image and the second slice that is a second MR image is 50, and thus the second slice that is the second MR image may be selected. Also, a variation 760 of the areas of the first regions of the 10th slice that is a first MR image and the 11th slice that is a second MR image is 60, and thus the 11th slice that is the second MR image may be selected. The second and 11th slices selected as such may be used to detect an apex MR image and a base MR image.

FIG. 8 is a diagram of marks 810 related to apex or base MR images detected from a plurality of short-axis MR images 800 obtained per predetermined time interval 860.

Referring to FIG. 8, the plurality of short-axis MR images 800 obtained per predetermined time interval 860 are displayed on one screen. The marks 810 may be identically or differently displayed according to an apex or a base. The marks 810 may be automatically displayed, and the displayed marks 810 may be manually changed by a user later to marks about other MR images. In the displayed plurality of short-axis MR images 800, the marks 810 for distinguishing apex or base MR images from other MR images may be displayed on the apex or base MR images. The short-axis MR images 800 obtained at a first time may be arranged in one column 820. An arrangement order 850 of the short-axis MR images 800 may be in the first direction 580 or the second direction 590 of FIG. 5 according to locations in the heart. Also, the plurality of MR images 800 in one row, for example, a row 830, may be MR images of the same region of an object obtained at the predetermined time interval 860.

According to an embodiment of the present invention, when the arrangement order 850 of the short-axis MR images 800 is in the first direction 580, an average of locations of the apex MR images may be a location corresponding to MR images in a row 840, and an average of locations of the base MR images may be a location corresponding to MR images in the row 830.

FIG. 9 is a diagram for describing changing of an apex or base MR image by comparing apex or base MR images detected from a plurality of short-axis MR images 900 obtained per predetermined time interval 960.

Referring to FIG. 9, according to an embodiment of the present invention, the plurality of short-axis MR images obtained per predetermined time interval 960 are displayed on one screen. The short-axis MR images 900 obtained at a first time may be arranged on one column. An arrangement order 950 may be in the first direction 580 or the second direction 590 of FIG. 5 according to locations in the heart. Also, a plurality of MR images included in one row, for example, a row 930, may be MR images of the same region in an object that are obtained per predetermined time interval 960. According to an embodiment of the present invention, when the arrangement order 950 is in the first direction 580, an average of locations of apex MR images may be a location corresponding to MR images in a row 940, and an average of locations of base MR images may be a location corresponding to MR images in the row 930. When locations of apexes or bases in the apex or base MR images are compared with an average location of apexes or bases in the apex or base MR images and there is an apex or base MR image whose location of an apex or base is different from the average location by a predetermined threshold value or higher, the location of the apex or base of such an apex or base MR image may be changed to the average location. Here, the predetermined threshold value may be a reference value for determining whether to change a location of an MR image detected at a predetermined time by comparing the location of the MR image detected at the predetermined time with an average location of the MR images detected over the certain period of time.

According to an embodiment of the present invention, when the predetermined threshold value is set to be a difference by two slices, an MR image 910 that is detected to be different from the row 930 that is the average location of the base MR images by three slices may be changed to an MR image 911 in the row 930 of the base MR images. Also, an MR image 920 that is detected be different from the row 940 that is the average location of the apex MR images by three slices may be changed to an MR image 921 in the row 940 of the apex MR images. Here, in order to prevent the average location of the apex MR images from being compared with a location of a base MR image, only a predetermined number of slices from the average location of the apex or base may be compared. Here, the predetermined number of slices may be changed by a user.

FIG. 10 is a flowchart of a method of detecting at least one of an apex MR image and a base MR image, according to an embodiment of the present invention.

In operation S1010, in the MR image processing apparatus 300 according to an embodiment of the present invention, the image processor 62 may obtain a plurality of MR images based on RF signals received by the signal transceiver 30. The signal transceiver 30 transmits or receives a signal to or from the heart. Here, the transmitted or received signal may be an RF signal transmitted or received through the RF transmitter 36 and the RF receiver 38, or raw data generated by using the RF signal. Here, the raw data may be k space data obtained by arranging the RF signal in a k space. Hereinafter, it is assumed that the signal transmitted or received by the signal transceiver 30 is an MR signal or an RF signal.

In detail, the signal transceiver 30 includes the RF receiver 38 of FIG. 1, and thus may directly receive an MR signal detected by the RF coil 26 of FIG. 1. Also, the signal transceiver 30 may be connected to the RF receiver 38 of FIG. 1 and may receive an MR signal from the RF receiver 38. According to an embodiment of the present invention, the received RF signal may be an RF signal about a short-axis of the heart of the object 10, or an MR signal about the short-axis and an RF signal about a long-axis, and in detail, may only include the RF signal about the short-axis.

In operation S1020, at least one contour may be determined from among the plurality of contours displayed on the plurality of MR images of the heart of the object 10.

According to an embodiment of the present invention, if the object 10 is the heart, a contour may be formed by a heart wall, and in detail, may include a contour indicated by a surface forming a left ventricle. In detail, a boundary corresponding to a heart muscle of the left ventricle may be distinguishably displayed on an MR image of the heart. Technology of determining and displaying only a region corresponding to a certain heart muscle, including a left ventricle, is used not only in one or more embodiments of the present invention, but also during the heart MR image analyzing process for determining a cardiac disorder. For example, a contour may be determined by segmenting a structure by using a probabilistic method considering a reference structure, or a plurality of contours related to separated or split ventricle segments may be determined by temporally observing the heart according to heartbeat cycles in order to measure desynchronization of a ventricle. However, a method of determining at least one contour is not limited thereto.

In operation S1030, first information about a first region formed by the at least one contour may be obtained. The first information may be about an area, a center point, an average brightness, a standard deviation of brightness, a shape, or a radius of the first region, and according to an embodiment, the first information is about the area of the first region.

In operation S1040, at least one of an apex MR image and a base MR image may be determined from the plurality of MR images obtained in operation S1010, based on the first information. The at least one of the apex MR image and the base MR image may be detected by comparing a variation of the first information about the first region obtained in operation S1030 with a predetermined value, for example, whether the variation is equal to or higher than a threshold value, as will be described in detail later.

FIG. 11 is a flowchart of a method of comparing a threshold value and a variation of first information about a first region so as to detect an apex MR image or a base MR image, according to an embodiment of the present invention.

Referring to FIG. 11, in operation S1110, first information about a first region formed by at least one contour determined from each of a plurality of MR images is obtained. The first information may be about an area, a center point, an average brightness, a standard deviation of brightness, a shape, or a radius of the first region. Also, for example, if the object 10 is the heart, a contour may be formed by a heart wall, and in detail, may include a contour indicated by a surface forming a left ventricle.

In operation S1120, the first information about the first region is compared between adjacent MR images when the plurality of MR images are arranged in an order of locations in the heart. In detail, the first information about the first region of a first MR image from among the plurality of MR images is compared with the information about the first region of a second MR image that is a following MR image adjacent to the first MR image in a first direction and in a second direction opposite to the first direction according to the locations in the heart.

In operation S1130, it is determined whether a variation between the first information about the first region of the first MR image and the first information about the first region of the second MR image is equal to or higher than a predetermined threshold value. The predetermined threshold value may be set according to a type of the first information to select an MR image to be detected.

In operation S1140, if the variation is equal to or higher than the predetermined threshold value, the second MR image is selected. The number of selected second MR images may be at least one, and an apex MR image and a base MR image may be detected based on the at least one second MR image.

In operation S1150, otherwise, if the variation is lower than the predetermined threshold value, the pieces of first information about the first region of adjacent MR images are compared with each other based on the first information about the first region of an MR image corresponding to a following location of the first MR image. In other words, the first MR image used in operation S1130 is changed to the second MR image, and the second MR image used in operation S1130 is changed to a following MR image adjacent to the second MR image. Operation S1150 is performed in each of the first and second directions.

FIG. 12 is a flowchart of a method of displaying a mark related to an apex or base MR image detected from a short-axis MR image, according to an embodiment of the present invention.

An MR image processing method according to an embodiment of the present invention may further include displaying at least one of an apex MR image and a base MR image and displaying at least one of a mark indicating an apex on the displayed at least one MR image and a mark indicating a base in the displayed at least one MR image. The mark may be identically or differently displayed according to an apex or a base. The mark may be automatically displayed, and the displayed mark may be manually changed by a user later to a mark another MR image.

Referring to FIG. 12, in operation S1210, a plurality of short-axis MR images may be obtained.

In operation S1220, at least one contour may be determined from a plurality of contours displayed on each of the plurality of short-axis MR images of the object 10. For example, if the object 10 is the heart, a contour may be formed by a heart wall, and in detail, may include a contour indicated by a surface forming a left ventricle.

In operation S1230, first information about a first region formed by the at least one contour may be obtained from each of the plurality of short-axis MR images. The first information may be about an area, a center point, an average brightness, a standard deviation of brightness, a shape, or a radius of the first region, and according to an embodiment of the present invention, the first information may be about the area of the first region. Hereinafter, it is assumed that the first information includes the area of the first region.

In operation S1240, at least one of an apex MR image and a base MR image may be detected from the plurality of short-axis MR images obtained in operation S1020, based on the first information about the first region. The detecting of the at least one of the apex MR image and the base MR image may be performed by comparing the first information about the first region with a predetermined standard, for example, whether the first information is equal to or higher than a threshold value.

In operation S1250, a mark related to the at least one of the apex MR image and the base MR image detected in operation S1240 may be displayed. The mark may be identically or differently displayed according to an apex or a base. The mark may be automatically displayed, and the displayed mark may be changed manually by a user later to a mark related to another MR image. Such a mark may be displayed on the at least one of the apex and base MR images while displaying the plurality of short-axis MR images including the at least one of the apex and base MR images, or may be displayed on another location separately from regions displaying the plurality of short-axis MR images, but is not limited thereto. The mark of the apex and the mark of the base may be the same or different from each other.

FIG. 13 is a flowchart of a method of changing a location of an apex or base MR image by comparing apex or base MR images detected from MR images obtained per predetermined time interval, according to an embodiment of the present invention.

Referring to FIG. 13, in operation S1310, at least one of an apex MR image and a base MR image is detected per predetermined time interval.

In operation S1320, a location of an apex or base MR image detected from a plurality of MR images obtained at a first time is compared with an average location of apex or base MR images obtained per predetermined time interval to determine a difference. The average location may be an average of locations of apex or base MR images detected during a total time the plurality of MR images are obtained, or an average of locations of apex or base MR images detected during some of the total time. The average location may be defined in an order of slices arranged when the plurality of MR images obtained per predetermined time interval are arranged in a first direction or a second direction according to locations in the heart.

In operation S1330, it is determined whether the difference determined in operation S1320 is equal to or higher than a predetermined threshold value. Here, the predetermined threshold value may be a reference value for determining whether to change a location of an MR image obtained per predetermined time interval by comparing the location of the MR image with an average location of MR images.

In operation S1340, if the difference is equal to or higher than the predetermined threshold value, the location of the apex or base MR image obtained at the first time is changed. The changed location may correspond to an average location of apex MR images obtained per predetermined time interval, or an arbitrary location between the average location and the location of the apex or base MR image obtained at the first time, but is not limited thereto.

In operation S1350, otherwise, if the difference is lower than the predetermined threshold value, the location of the apex or base MR image obtained at the first time is not changed.

FIG. 14 is a flowchart of a method of generating a long-axis MR image by using a short-axis MR image and displaying a mark on a region of the long-axis MR image corresponding to a short-axis apex MR image or a short-axis base MR image detected from the short-axis MR image.

Referring to FIG. 14, in operation S1410, in the MR image processing apparatus 300 according to an embodiment of the present invention, the image processor 62 may obtain short-axis MR images of the heart of the object 10 based on an RF signal received by the signal transceiver 30.

In operation S1420, at least one contour may be determined from a plurality of contours displayed on each of the plurality of short-axis MR images of the heart of the object 10. According to an embodiment of the present invention, if the object 10 is the heart, a contour may be formed by a heart wall, and in detail, may include a contour indicated by a surface forming a left ventricle. In detail, a boundary corresponding to a heart muscle of the left ventricle may be distinguishably displayed on a short-axis MR image of the heart. Technology of determining and displaying only a region corresponding to a certain heart muscle including a left ventricle is used not only in one or more embodiments of the present invention, but also during the heart MR image analyzing process for determining a cardiac disorder. For example, a contour may be determined by segmenting a structure by using a probabilistic method considering a reference structure, or a plurality of contours related to separated or split ventricle segments may be determined by temporally observing the heart according to heartbeat cycles in order to measure desynchronization of a ventricle. However, a method of determining at least one contour is not limited thereto.

In operation S1430, first information about a first region formed by the at least one contour may be obtained. The first information may be about an area, a center point, an average brightness, a standard deviation of brightness, a shape, or a radius of the first region. According to an embodiment of the present invention, the first information may be about the area of the first region, and hereinafter, it is assumed that the first information includes the area of the first region.

In operation S1440, at least one of a short-axis apex MR image and a short-axis base MR image may be detected from the plurality of short-axis MR images obtained in operation S1410, based on the first information. The detecting of the at least one of the short-axis apex MR image and the short-axis base MR image may be performed by comparing a variation of the first information about the first region with a predetermined standard (for example, whether the variation is equal to or higher than a threshold value), in the similar manner described above with reference to FIG. 11.

In operation S1450, at least one long-axis MR image of the heart of the object 10 may be generated via a predetermined calculation based on the plurality of short-axis MR images obtained in operation S1410. A long-axis of the heart may be an axis parallel to a plane perpendicular to a short-axis, and in detail, may be an axis from a spleen of the object 10 to a right shoulder.

In operation S1460, a mark may be displayed on a region of the at least one long-axis MR image generated in operation S1450, which corresponds to the short-axis apex or base MR image detected in operation S1440, when the at least one long-axis MR image is displayed. The mark may be identically or differently displayed according to an apex or a base. The mark may be automatically displayed, and the displayed mark may be manually changed by a user later to a mark related to another MR image.

The embodiments of the present invention can be written as computer programs and can be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs or DVDs), etc.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A computer-implemented magnetic resonance (MR) image processing method for processing an MR image of a heart, the computer-implemented MR image processing method comprising:
   determining at least one contour from each of a plurality of MR images obtained by photographing the heart via magnetic resonance imaging (MRI);
   obtaining first information about a first region formed by the at least one contour; and
   detecting at least one of an apex MR image and a base MR image of the heart from among the plurality of MR images based on the first information;
   wherein the detecting the at least one of the apex MR image and the base MR image comprises detecting the at least one of the apex MR image and the base MR image per a redetermined time interval, and
   wherein the computer-implemented MR image processing method further comprises, if a location of an apex MR image obtained at a first time is different, from an average of locations of apex MR images obtained per predetermined time interval by a predetermined threshold value or higher, changing the location of the apex MR image obtained at the first time.

2. The computer-implemented MR image processing method of claim 1, wherein the plurality of MR images are obtained by performing the MRI along a short-axis of the heart, and are MR images of a short-axis cross-section of the heart.

3. The computer-implemented MR image processing method of claim 2, wherein the obtaining of the first information comprises obtaining the first information about an area of the first region from the plurality of MR images, respectively, and when the plurality of MR images are arranged and compared according to locations in the heart based on the first information, selecting at least one second MR image when a variation between the area of the first region of a first MR image and the area of the first region of the second MR image that is a following MR image adjacent to the first MR image among the plurality of MR images is equal to or higher than a threshold value.

4. The computer-implemented MR image processing method of claim 3, wherein the detecting the at least one of the apex MR image and the base MR image comprises arranging the plurality of MR images according to locations in the heart and comparing the plurality of MR images in a first direction and a second direction opposite to the first direction of an arranged order to detect a second MR image that is initially selected from among the at least one second MR image in each of the first direction and the second direction.

5. The computer-implemented MR image processing method of claim 2, further comprising displaying at least one of the apex MR image and the base MR image.

6. The computer-implemented MR image processing method of claim 2, wherein the plurality of MR images obtained by performing the MRI along the short-axis of the heart comprise the MR images obtained by imaging a same location of the heart per the predetermined time interval.

7. The computer-implemented MR image processing method of claim 6, further comprising:
if a location of a base MR image obtained at the first time is different from an average of locations of base MR images obtained per the predetermined time interval by a predetermined threshold value or higher, changing the location of the base MR image obtained at the first time.

8. A magnetic resonance (MR) image processing apparatus for processing an MR image of a heart, the MR image processing apparatus comprising:
a signal transceiver that transmits and receives a signal to and from the heart; and
an image processor configured to:
obtain a plurality of MR images of the heart by using the received signal,
determine at least one contour from each of the plurality of MR images;
obtain first information about a first region formed by the at least one contour, and
detect at least one of an apex MR image and a base MR image of the heart from among the plurality of MR images based on the first information,
wherein the image processor is further configured to:
detect the at least one of the apex MR image and the base MR image per a predetermined time interval, and
if a location of an apex MR image obtained at a first time is different from an average of locations of apex MR images obtained per the predetermined time interval by a predetermined threshold value or higher, change the location of the apex MR image obtained at the first time.

9. The MR image processing apparatus of claim 8, wherein the image processor is further configured to obtain the plurality of MR images by performing an MR imaging (MRI) along a short-axis of the heart, and
wherein the plurality of MR images are MR images of a short-axis cross-section of the heart.

10. The MR image processing apparatus of claim 9, wherein the image processor is further configured to obtain the first information based on an area of the first region from the plurality of MR images, and, when the plurality of MR images are arranged and compared according to locations in the heart based on the first information, select at least one second MR image when a variation between the area of the first following MR image adjacent to the first MR image among the plurality of MR images is equal to or higher than a threshold value.

11. The MR image processing apparatus of claim 10, wherein, when the plurality of MR images are arranged according to locations in the heart and the plurality of MR images are compared in a first direction and a second direction opposite to the first direction of an arranged order, the apex MR image or the base MR image is a second MR image that is initially selected from among the at least one second MR image in each of the first direction and the second direction.

12. The MR image processing apparatus of claim 9, further comprising a display that displays the plurality of MR images comprising at least one of the apex MR image and the base MR image.

13. The MR image processing apparatus of claim 9, wherein the image processor is further configured to obtain the plurality of MR images along the short-axis of the heart imaging a same location of the heart per a predetermined time interval.

14. The MR image processing apparatus of claim 13, wherein, in detecting the at least one among the apex MR image and the base MR image, the image processor is further configured to, if a location of a base MR image obtained at the first time is different from an average of locations of base MR images obtained per the predetermined time interval by a predetermined threshold value or higher, change the location of the base MR image obtained at the first time.

15. A non-transitory computer-readable recording medium having recorded thereon a program which, when executed by a computer, causes the computer to execute the computer-implemented MR image processing method of claim 1.

* * * * *